US005681855A

United States Patent [19]
Schütz et al.

[11] Patent Number: 5,681,855
[45] Date of Patent: Oct. 28, 1997

[54] PGE₁ EMULSION COMPOSITION KIT

[75] Inventors: Andreas Schütz, Köln; Hans-Jürgen Mika, Bonn; Frank Sievert, Burscheid, all of Germany

[73] Assignee: Schwarz Pharma AG, Germany

[21] Appl. No.: 535,001

[22] PCT Filed: Mar. 19, 1994

[86] PCT No.: PCT/DE94/00325

§ 371 Date: Sep. 21, 1995

§ 102(e) Date: Sep. 21, 1995

[87] PCT Pub. No.: WO94/21263

PCT Pub. Date: Sep. 29, 1994

[30] Foreign Application Priority Data

Mar. 24, 1993 [DE] Germany ............ 43 09 579.8

[51] Int. Cl.⁶ .................................. A61K 31/19
[52] U.S. Cl. ............ 514/559; 514/560; 514/23; 514/78; 514/529; 514/573; 514/738; 514/937; 514/970
[58] Field of Search ............ 514/559, 560, 514/23, 78, 529, 573, 738, 937, 970

[56] References Cited

U.S. PATENT DOCUMENTS 4,684,633  8/1987  Imagawa et al. .................. 514/78

FOREIGN PATENT DOCUMENTS

| 0 150 732 A2 | 8/1985 | European Pat. Off. . |
| 0 161 445 A1 | 11/1985 | European Pat. Off. . |
| 0 331 755 A1 | 9/1989 | European Pat. Off. . |
| 28 18 655 A1 | 11/1978 | Germany . |
| 41 25 255 A1 | 2/1993 | Germany . |
| 53-148 518 A | of 0000 | Japan . |
| 57-156 460 A | of 0000 | Japan . |
| 61-100 518 A | of 0000 | Japan . |
| A 05043450 | 2/1993 | Japan . |
| WO 91/11172 | 8/1991 | WIPO . |

OTHER PUBLICATIONS

The United States Pharmacopeia, The National Formulary, USP 23, NF 18, 1995, pp. 2241, 2269.

*Primary Examiner*—Rebecca Cook
*Attorney, Agent, or Firm*—Merchant, Gould, Smith, Edell, Welter & Schmidt, P.A.

[57]  ABSTRACT

The invention concerns a kit for the preparation of an emulsion containing prostaglandin $E_1$, a method of preparing the emulsion and a method of preparing the emulsion composition contained in the kit. The emulsion prepared using this kit is suitable for parenteral application.

12 Claims, No Drawings

PGE$_1$ EMULSION COMPOSITION KIT

DESCRIPTION

The present invention relates to a kit for the preparation of a fat emulsion which contains prostaglandin E$_1$ (PGE$_1$) for direct parenteral use.

In particular, the invention relates to a kit consisting of
a) an anhydrous, lyophilized PGE$_1$-containing emulsion composition
b) an aqueous dispersion medium and
c) a filter
for the preparation of a PGE$_1$-containing fat emulsion, which is ready for administration, by mixing, and extruding through the filter c), the anhydrous, lyophilized PGE$_1$-containing emulsion composition a) with the aqueous dispersion medium b).

PGE$_1$ is a highly active tissue hormone which is successfully used, for example, for the treatment of arterial occlusive disease. Used for this purpose is a PGE$_1$-α-cyclodextrin complex which, dissolved in physiological saline solution, is infused parenterally, preferably intraarterially, as close as possible to the body region to be treated. However, high pressure conditions and small dilution effects during the intraarterial infusion make high demands on the equipment and the training of the treating physician. Although intravenous infusion is simpler to perform by comparison, even in this case infusion is possible only slowly and in relatively high dilution because of the local irritant effect of PGE$_1$. Overall, the extended residence time of the active substance in the vascular system before reaching the target site and, in particular, the additional passage through the pulmonary circulation leads to increased degradation of active substance. Both intraarterial and intravenous infusions make high demands on the equipment and careful adjustment of the infusion rate and are therefore usually performed in hospital and not by the established physician, which impedes wide use of the valuable active substance in the therapy of arterial occlusive disease.

Fat emulsions are disperse systems in which the internal, disperse phase consists of very fine fat particles which are homogeneously dispersed in the external, continuous phase composed of water.

As a predominantly lipophilic substance, PGE$_1$ can be partly or completely incorporated into the internal phase of fat emulsions, from which it is then released in a delayed manner. This avoids high local concentrations, degradation of the active substance is reduced and the duration of action is increased so that incorporation into fat emulsions is suitable for overcoming the problems described.

PGE$_1$-containing fat emulsions for parenteral use can be prepared by dissolving PGE$_1$ in the oil phase which is subsequently processed further in accordance with a customary preparation process to give a fat emulsion. This can take place, for example, by the heated oil and water phases initially being roughly preemulsified with a mixer and then microfine emulsification being carried out with a high-pressure homogenizer, and the resulting fat emulsion subsequently being sterilized with superheated steam. Microfine emulsification is necessary in order to avoid changes in blood pressure and the risk of embolism as a consequence of large fat particles. Although such PGE$_1$-containing fat emulsions are suitable for solving the described disadvantages of the conventional use of PGE$_1$, their storage stability is low as a consequence of hydrolytic degradation of the active substance, which impedes their general utilizability.

According to U.S. Pat. No. 4,684,633, a fat emulsion which contains prostaglandins and consists of vegetable oils, phospholipids and water can be stabilized by using phospholipids which have been freed of phosphatidylethanolamine. However, stabilization of the active substance is shown only for the condition of brief sterilization at 125° C. for 2.2 min. Data on the stability on long-term storage are lacking. The formulation also contains water so that degradation of active substance as a consequence of hydrolysis cannot be ruled out in principle.

Besides stabilization of the active substance in a fat emulsion ready for administration, fat emulsions containing intact active substance can also be used by preparing them only immediately before use. One example of this is given in EP 0 331 755, consisting of active substance, saccharides and/or amino acids, which are combined and vigorously mixed immediately before use. Vigorous mixing is absolutely necessary in order to make it possible to disperse the active substance in the fat emulsion. However, long mixing times are disadvantageous on use.

An example relating to prostaglandins which is mentioned in EP 0 331 755, Example 3, describes an active substance composition consisting of a prostaglandin and triethanolamine. However, triethanolamine is not without objections physiologically so that its use in pharmaceutical formulations, especially in injectable products, should be avoided where possible.

Thus there continued to be A need for a possibility, which can be handled simply and rapidly, for using a PGE$_1$-containing fat emulsion. It ought fundamentally to preclude hydrolysis of the active substance during storage owing to absence of water, use only physiologically acceptable auxiliary substances and avoid long preparation and equilibration times before use.

It has been possible to close this gap in the state of the art by making available a kit for a PGE$_1$-containing emulsion which can be used and consists of
a) an anhydrous, lyophilized PGE$_1$-containing emulsion composition
b) an aqueous dispersion medium and
c) a filter.

In this case PGE$_1$ is contained in an anhydrous emulsion composition so that degradation of active substance as a consequence of hydrolysis is fundamentally ruled out, and dispersion in the fat phase of the emulsion is ensured from the outset.

The PGE$_1$-containing emulsion composition contained in the kit advantageously contains at least one cryoprotection agent and/or at least one bulking agent, a polar fat, a phospholipid and/or a hydrophilic emulsifier. Polar fats are glycerides whose hydroxyl groups, besides higher fatty acids, are also esterified with short-chain carboxylic acids or are unesterified in free form and, in contrast to triglycerides with higher fatty acids, have a certain affinity for polar solvents. Hydrophilic emulsifiers are surfactants whose emulsifying behaviour is crucially determined by their hydrophilic groups and preferentially form fat-in-water emulsions.

The PGE$_1$-containing emulsion composition contained in the kit preferably contains acetylated monoglycerides, glycerol phosphatides and/or polyoxyethylene polyoxypropylene polymers.

The anhydrous PGE$_1$-containing emulsion composition contained in the kit particularly preferably contains diacetylated monoglycerides, phosphatidylcholine and/or poloxamer 188.

According to an expedient embodiment, the fat component(s) and the emulsifier(s) are present in a ratio of 1:2 to 10:1 by weight, preferably in a ratio of 3:2 by weight.

According to another expedient embodiment, the phospholipid and the hydrophilic emulsifier are present in a ratio of 3:1 to 1:2 by weight, preferably in a ratio of 3: 2 by weight.

According to an advantageous embodiment, the anhydrous $PGE_1$-containing emulsion composition contained in the kit contains as cryoprotection agents/bulking agents physiologically tolerated mono-, di- or oligosaccharides, especially trehalose and lactose and/or sugar alcohols such as sorbitol or mannitol.

According to a particularly expedient embodiment, the kit for a $PGE_1$-containing emulsion which can be used contains a filter which is a membrane filter with a pore size of 0.5–1.3 μm, preferably 0.8 μm, or a corresponding deep-bed filter. Preferred in this connection are commercially available devices in which the filter is firmly integrated between cannula and fit-on connector.

According to a preferred embodiment, the anhydrous $PGE_1$-containing emulsion composition contained in the kit contains at least one conventional antioxidant, in particular from the group of tocopherols such as $\alpha$-, $\beta$-, $\gamma$- or $\delta$-tocopherol, preferably $\alpha$-tocopherol, and physiologically tolerated salts thereof, such as phosphates, succinates and acetates and/or physiologically tolerated buffer salts.

According to a particularly preferred embodiment, the internal phase of the emulsion which can be used and is prepared with the kit has an average particle diameter of 0.1 μm to 5 μm, preferably 0.5 μm to 2.0 μm.

The emulsion composition contained in the kit according to the invention can be prepared by removing the aqueous phase by lyophilization from an emulsion which has been prepared by the processes and technologies customary in the production of pharmaceuticals.

The invention therefore also relates to a process for the preparation of the anhydrous $PGE_1$-containing emulsion composition contained in the kit according to the invention, which is characterized in that an emulsion containing an active substance is prepared in a conventional way and its external, aqueous phase is subsequently removed by freeze-drying.

It is possible with the kit according to the invention to prepare in a simple manner a $PGE_1$-containing emulsion which can be used, i.e. is suitable for direct parenteral administration.

It therefore furthermore relates to a process for the preparation of a $PGE_1$-containing emulsion, which can be used, by means of the kit according to the invention, which is characterized in that the hydrous $PGE_1$-containing emulsion composition a) is mixed with the aqueous dispersion medium b) and extruded through the filter c).

Example 2.8 g of poloxamer 188 and 40.0 g of trehalose were dissolved by heating in 320 g of water for injections. Subsequently 4.00 g of phosphatidyldholine, 13.0 g of diacetylated monoglycerides, 0.20 g of $\alpha$-tocopherol were dissolved in 20.0 g of absolute ethanol with gentle heating and under an inert atmosphere.

The aqueous phase was transferred into a suitable presterilized reaction vessel (IKA LR-A 1000 laboratory reactor, Jahnke & Kunkel GmbH, Staufen, Germany) with temperature-control device, stirrer tool and toothed rim disperser ( Ultraturrax, Jahnke & Kunkel μmbH, Staufen, Germany) and heated to 80° C. while stirring under a vacuum of<1 mbar. While maintaining the vacuum and the stirring, the ethanolic emulsifier lipid phase was injected directly into the aqueous phase with vigorous homogenization using the Ultraturrax. The mixture was subsequently cooled, with continuous stirring and maintenance of the vacuum, to room temperature while vigorous homogenization was carried out using the toothed rim dispersing rod for about 1 min in several periods. To incorporate the active substance, 131.6 mg of $PGE_1$-$\alpha$-cyclodextrin complex were added to the cooled emulsion. The resulting emulsion containing active substance was sterilized by filtration and transferred under aseptic conditions using a Dispensette with a capacity of 2 ml per single dose to a height of about 1 cm into presterilized vials. After charging, the vials were provided with stoppers, placed in the lyophilizer and frozen at −50° C. for 5 hours. The subsequent lyophilization process was carried out as shown in the following table:

| Time (hours) | Temperature (°C.) | Pressure (μbar) |
|---|---|---|
| 24 | −30 | 100 |
| 10 | 20 | 1 |

Subsequently the vacuum was removed with simultaneous introduction of nitrogen, the vials were closed by hydraulic lowering of the stoppers and were removed from the lyophilizer under aseptic conditions after it had been opened.

After addition of water, the product cakes contained in them disintegrated spontaneously to give a homogeneous emulsion. This was removed using a syringe through a membrane filter which was located between the latter and the cannula and had a pore size of 0.8 pro, and was investigated for its particle sizes (volume distribution) (method: laser light scattering; Malvern Master Sizer, Series 3.01, Malvern Instruments Ltd., Spring Lane, South Malvern, Worcestershire, WR14 1AQ, UK).

The measurement showed that 99.9% of all the particles are<4.10 μm, no particle is>5.64 μm and the average particle size is 1.15 μm. The present emulsion thus has a particle size distribution suitable for parenteral administration.

We claim:

1. A kit for the parenteral administration of prostaglandin $E_1$ ($PGE_1$) comprising
    a) an anhydrous, lyophilized $PGE_1$ emulsion composition, comprising:
        at least one cryoprotection agent:
        a polar fat which is an acetylated monoglyceride
        a phospholipid; and
        a hydrophilic emulsifier;
    b) an aqueous dispersion medium, and
    c) a filter.

2. The kit of claim 1 wherein the phospholipid is a glycerol phosphatide, and the hydrophilic emulsifier is a polyoxyethylene polyoxypropylene polymer.

3. The kit of claim 1, wherein the polar fat is a diacetylated monoglyceride; the phospholipid is phosphatidylcholine, and the hydrophilic emulsifier is poloxamer 188.

4. The kit of claim 1, wherein at least one fat and at least one emulsifier are present in a ratio of about 1:2 to 10:1 by weight.

5. The kit of claims 1, wherein the phospholipid and the hydrophilic emulsifier are present in a ratio of about 3:1 to 1:2 by weight.

6. The kit of claim 1, wherein the cryoprotection agent is at least one member selected from the group consisting of a physiologically tolerated mono-, di- or oligosaccharide and a sugar alcohol, or a mixture thereof.

7. The kit of claim 6, wherein the saccharide is at least one member selected from the group consisting of trehalose and lactose, and the sugar alcohol is at least one member selected from the group consisting of sorbitol and mannitol.

8. The kit of claim 1, wherein the filter is a membrane filter with a pore size of about 0.5–1.3 µm, or a corresponding deep-bed filter.

9. The kit of claim 1, wherein the emulsion composition further comprises at least one antioxidant, a physiologically tolerated salt thereof, a physiologically tolerated buffer salt or a mixture thereof.

10. The kit of claim 9 wherein the antioxidant is $\alpha, \beta, \gamma$ or $\delta$-tocopherol or a physiologically tolerated salt thereof.

11. The kit of claim 10, wherein the physiologically tolerated salt is a phosphate, succinate, or acetate.

12. The kit of claim 1, wherein the internal, disperse phase of the emulsion has an average particle diameter of about 0.1 µm to 5 µm.

* * * * *

UNITED STATES PATENT AND TRADEMARK OFFICE
CERTIFICATE OF CORRECTION

PATENT NO. : 5,681,855

DATED : October 28, 1997

INVENTOR(S) : Andreas Schutz et al.

It is certified that error appears in the above-identified patent and that said Letters Patent is hereby corrected as shown below:

On column 3, line 60, please delete "phosphatidyldholine" and substitute therefore --phosphatidylcholine--

On column 4, line 2, please delete "umbH" and substitute therefore --GmbH--

On column 4, line 39, please delete "pro" and substitute therefore --μm--

On column 5, line 4 (claim 5), please delete "claims" and substitute therefore --claim--

Signed and Sealed this

Thirtieth Day of June, 1998

*Attest:*

BRUCE LEHMAN

*Attesting Officer*   *Commissioner of Patents and Trademarks*